(12) United States Patent
Hall

(10) Patent No.: US 6,257,252 B1
(45) Date of Patent: Jul. 10, 2001

(54) FLOSSING DEVICE AND METHOD

(76) Inventor: Sylvester B. Hall, 10000 US Hwy. 98 North # 272, Lakeland, FL (US) 33809

( * ) Notice: Subject to any disclaimer, the term of this patent is extended or adjusted under 35 U.S.C. 154(b) by 0 days.

(21) Appl. No.: 09/627,478

(22) Filed: Jul. 28, 2000

(51) Int. Cl.$^7$ .................................................. A61C 15/00
(52) U.S. Cl. ............................................................ 132/323
(58) Field of Search .................................. 132/323, 324, 132/325, 326, 327; D28/65, 66, 67, 68

(56) References Cited

U.S. PATENT DOCUMENTS

| | | | |
|---|---|---|---|
| D. 237,499 | * | 11/1975 | Maloney et al. ..................... D28/68 |
| D. 240,831 | * | 8/1976 | Wang ..................................... D28/68 |
| D. 241,647 | * | 9/1976 | Ruggieri ............................... D28/68 |
| D. 299,977 | * | 2/1989 | Rinaudo ................................ D28/68 |
| D. 323,723 | * | 2/1992 | Chung .................................... D28/68 |
| D. 401,701 | | 11/1998 | Chodorow . |
| 1,512,633 | * | 10/1924 | Peckham ............................. 132/325 |
| 2,354,454 | * | 7/1944 | Geffner ............................... 132/323 |
| 2,664,093 | * | 12/1953 | Carpenter ............................ 132/323 |
| 3,939,853 | | 2/1976 | Spanondis . |
| 4,671,307 | * | 6/1987 | Curbow et al. ..................... 132/323 |
| 5,280,797 | | 1/1994 | Fry . |
| 5,823,207 | | 10/1998 | Bushman . |
| 5,878,759 | | 3/1999 | Arias . |
| 5,881,744 | | 3/1999 | Lo . |
| 5,940,923 | * | 8/1999 | Gunning .............................. 132/323 |

FOREIGN PATENT DOCUMENTS

2007982 * 5/1979 (GB) ................................... 132/323

* cited by examiner

Primary Examiner—Jeffrey A. Smith
Assistant Examiner—Eduardo C. Robert

(57) ABSTRACT

A flossing device for holding floss to floss teeth with. The flossing device includes an arm. The arm has a middle portion, a distal portion and a proximal portion. The arm has a top side and a bottom side. A straight head portion comprises a base portion and two legs integrally coupled to and extending away from the base portion. The base portion is integrally coupled to a free end of the distal portion. The straight head portion has a pair of outer peripheral edges. Each of the outer peripheral edges has an elongate slot therein. A securing structure releasably secures the floss in the slots of the straight head portion.

8 Claims, 2 Drawing Sheets

FLOSSING DEVICE AND METHOD

BACKGROUND OF THE INVENTION

1. Field of the Invention

The present invention relates to flossing devices and more particularly pertains to a new flossing device for holding floss to floss teeth with.

2. Description of the Prior Art

The use of flossing devices is known in the prior art. More specifically, flossing devices heretofore devised and utilized are known to consist basically of familiar, expected and obvious structural configurations, notwithstanding the myriad of designs encompassed by the crowded prior art which have been developed for the fulfillment of countless objectives and requirements.

Known prior art includes U.S. Pat. No. 5,280,797; U.S. Pat. No. 5,881,744; U.S. Pat. No. 5,878,759; U.S. Pat. No. 5,823,207; U.S. Pat. No. 401,701; and U.S. Pat. No. 3,939,853.

While these devices fulfill their respective, particular objectives and requirements, the aforementioned patents do not disclose a new flossing device. The inventive device includes an arm. The arm has a middle portion, a distal portion and a proximal portion. The arm has a top side and a bottom side. A straight head portion comprises a base portion and two legs integrally coupled to and extending away from the base portion. The base portion is integrally coupled to a free end of the distal portion. The straight head portion has a pair of outer peripheral edges. Each of the outer peripheral edges has an elongate slot therein. A securing means for releasably secures floss in the slots of the straight head portion.

In these respects, the flossing device according to the present invention substantially departs from the conventional concepts and designs of the prior art, and in so doing provides an apparatus primarily developed for the purpose of holding floss to floss teeth with.

SUMMARY OF THE INVENTION

In view of the foregoing disadvantages inherent in the known types of flossing devices now present in the prior art, the present invention provides a new flossing device construction wherein the same can be utilized for holding floss to floss teeth with.

The general purpose of the present invention, which will be described subsequently in greater detail, is to provide a new flossing device apparatus and method which has many of the advantages of the flossing devices mentioned heretofore and many novel features that result in a new flossing device which is not anticipated, rendered obvious, suggested, or even implied by any of the prior art flossing devices, either alone or in any combination thereof.

To attain this, the present invention generally comprises an arm. The arm has a middle portion, a distal portion and a proximal portion. The arm has a top side and a bottom side. A straight head portion comprises a base portion and two legs integrally coupled to and extending away from the base portion. The base portion is integrally coupled to a free end of the distal portion. The straight head portion has a pair of outer peripheral edges. Each of the outer peripheral edges has an elongate slot therein. A securing means for releasably secures floss in the slots of the straight head portion.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new flossing device apparatus and method which has many of the advantages of the flossing devices mentioned heretofore and many novel features that result in a new flossing device which is not anticipated, rendered obvious, suggested, or even implied by any of the prior art flossing devices, either alone or in any combination thereof.

It is another object of the present invention to provide a new flossing device which may be easily and efficiently manufactured and marketed.

It is a further object of the present invention to provide a new flossing device which is of a durable and reliable construction.

An even further object of the present invention is to provide a new flossing device which is susceptible of a low cost of manufacture with regard to both materials and labor, and which accordingly is then susceptible of low prices of sale to the consuming public, thereby making such flossing device economically available to the buying public.

Still yet another object of the present invention is to provide a new flossing device which provides in the apparatuses and methods of the prior art some of the advantages thereof, while simultaneously overcoming some of the disadvantages normally associated therewith.

Still another object of the present invention is to provide a new flossing device for holding floss to floss teeth with.

Yet another object of the present invention is to provide a new flossing device which includes an arm. The arm has a middle portion, a distal portion and a proximal portion. The arm has a top side and a bottom side. A straight head portion comprises a base portion and two legs integrally coupled to and extending away from the base portion. The base portion is integrally coupled to a free end of the distal portion. The straight head portion has a pair of outer peripheral edges. Each of the outer peripheral edges has an elongate slot therein. A securing means for releasably secures floss in the slots of the straight head portion.

Still yet another object of the present invention is to provide a new flossing device that holds floss so that a small amount of floss may be used to floss teeth.

Even still another object of the present invention is to provide a new flossing device that has two heads for reaching both the front and back teeth.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be made to the accompanying drawings and descriptive matter in which there are illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

DESCRIPTION OF THE PREFERRED EMBODIMENT

Figure 1:
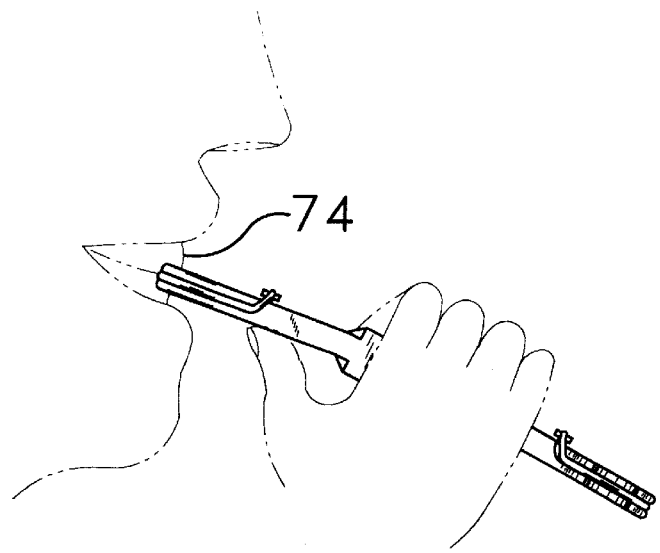
FIG. 1 is a schematic side view of a new flossing device according to the present invention.
Figure 2:
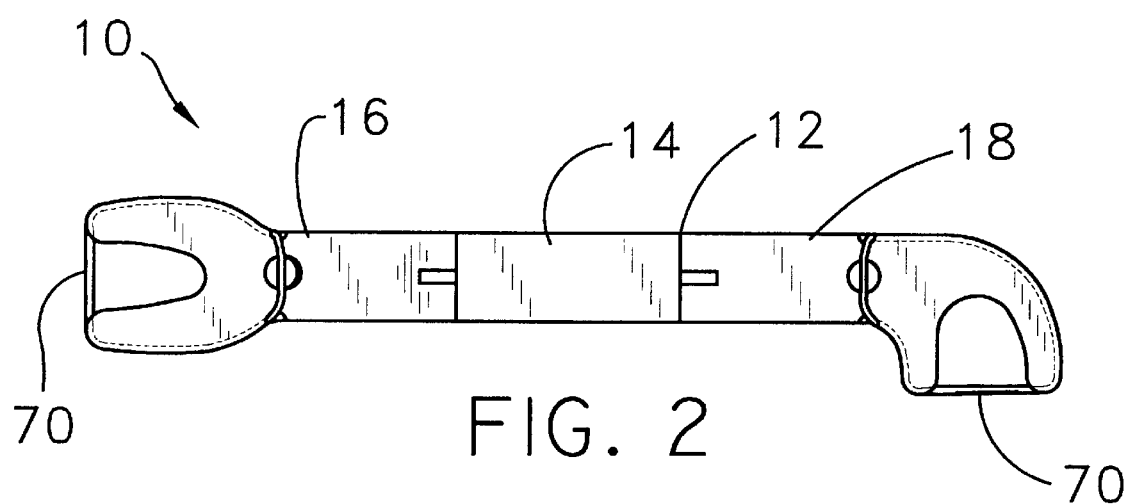
FIG. 2 is a schematic plan view of the present invention.
Figure 3:
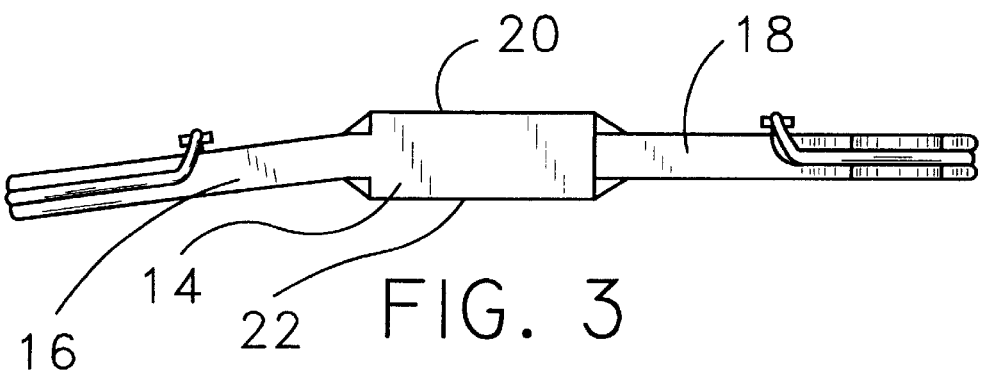
FIG. 3 is a schematic side view of the present invention.
Figure 4:
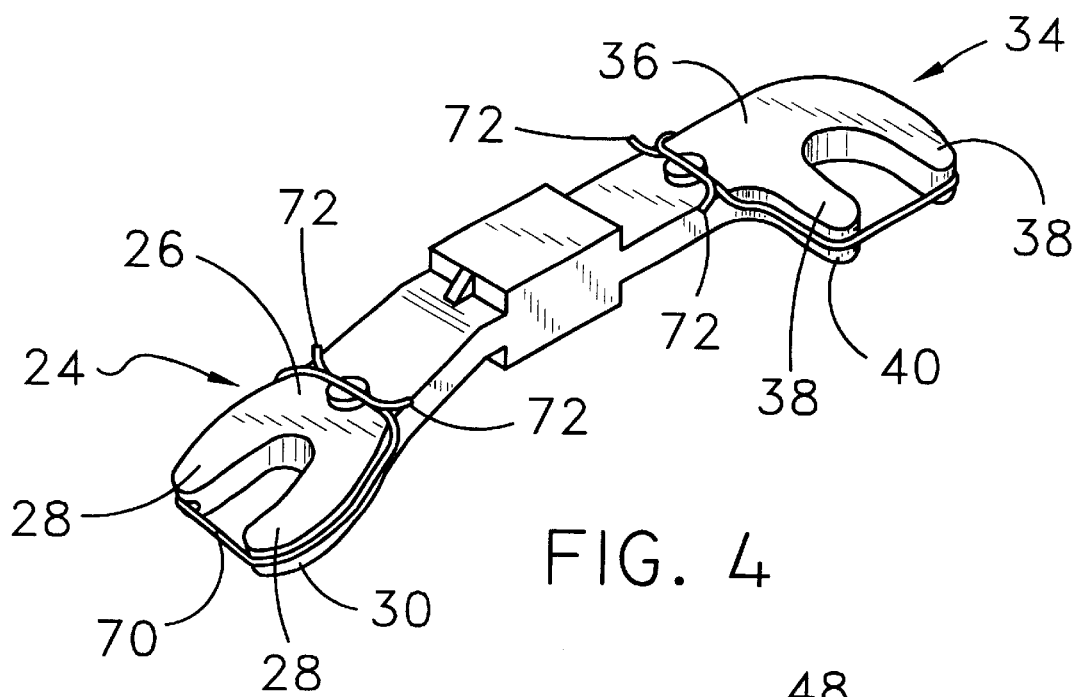
FIG. 4 is a schematic perspective view of the present invention.
Figure 5:
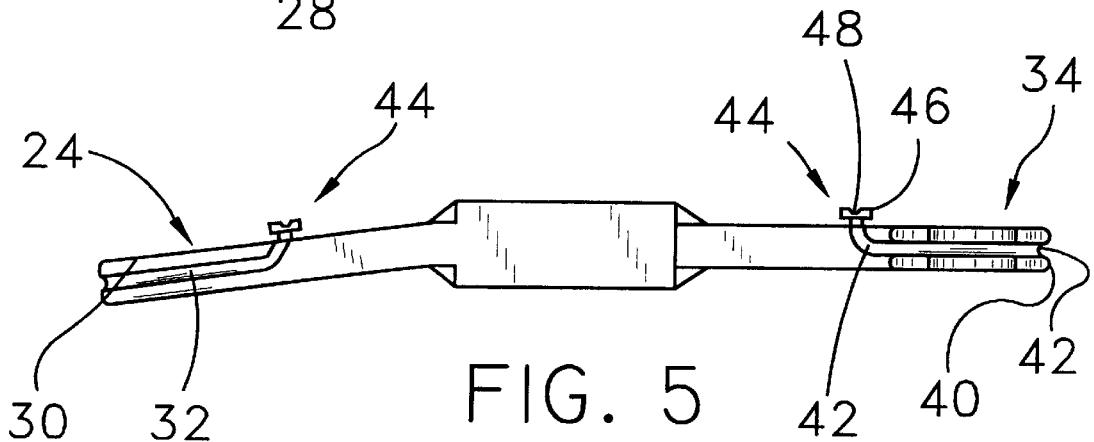
FIG. 5 is a schematic side view of the present invention.

With reference now to the drawings, and in particular to FIGS. 1 through 5 thereof, a new flossing device embodying the principles and concepts of the present invention and generally designated by the reference numeral 10 will be described.

As best illustrated in FIGS. 1 through 5, the flossing device 10 generally comprises providing an arm 12. The arm 12 has a middle portion 14, a distal portion 16 and a proximal portion 18. The arm 12 has a top side 20 and a bottom side 22. The distal portion 16 is in an angular relationship with the middle portion 14 such that an angle formed between the top sides of the middle 14 and distal 16 portions is generally between 150 degrees and 175 degrees. The middle portion may have a relatively greater height than the distal and proximal portions. In one embodiment of the invention, the height of the middle portion is generally greater than twice the height of the distal and proximal portions.

A straight head portion 24 comprises a base portion 26 and two legs 28 integrally coupled to and extending away from the base portion 26. The base portion 26 is integrally coupled to a free end of the distal portion 16. The legs 28 of the straight head portion are preferably orientated generally parallel to a longitudinal axis of the arm 12. The straight head portion 24 has a pair of outer peripheral edges 30. Each of the outer peripheral edges 30 has an elongate slot 32 therein. Each of the slots 32 extends from the free end of the distal portion 16 and around a free end of the legs 28. The distance between free ends of the legs 28 is preferably between ½ inch and ¾ inch and is ideally 9/16 inch.

A bent head portion 34 comprises a base wall 36 and two arms 38 integrally coupled to and extending away from the base wall 36. The base wall 36 is integrally coupled to a free end of the proximal portion 18. The arms 38 of the bent head portion 34 are orientated generally perpendicular to a longitudinal axis of the arm 12. The bent head portion 34 has a pair of outer perimeter edges 40. Each of the outer perimeter edges 40 has an elongate slot 42 therein. Each of the slots 42 in the outer perimeter edges 40 extends from the free end of the proximal portion 18 and around a free end of the arms 38. A distance between the arms 38 is generally between ½ and ¾ inches and is ideally ⅝ inch.

A securing means 44 releasably secures floss 70 in the bent 34 and straight 24 head portions. The securing means 44 comprises a pair of protruding members 46. Each of the protruding members 46 is securely attached to the top side 20 of the arm 12. Each of the protruding members 46 is positioned generally adjacent to one of the head portions 24, 34. Each of the protruding members 46 has a top end having a channel 48 therein for releasably engaging the floss 70.

In use, each of a pair of floss portions 70 is wrapped about a pair of oppositely disposed slots 32, 42 on one of the head portions 24, 34. Opposite ends 72 of the floss 70 are positioned through the channel 48 in a respective securing means 44. The teeth 74 are flossed with the portions of the floss 70 extending between the free ends of the arms 38 and the legs 28.

As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A tooth flossing device for holding a portion of tooth floss, said device comprising:

an arm having a middle portion, a distal portion and a proximal portion, said arm having a top side and a bottom side;

a straight head portion comprising a base portion and two legs integrally coupled to and extending away from said base portion, said base portion being integrally coupled to a free end of said distal portion, said straight head portion having a pair of outer peripheral edges, each of said outer peripheral edges having an elongate slot therein; and a first securing means for releasably securing said floss in said slots of said straight head portion;

a bent head portion comprising a base wall and two arms integrally coupled to and extending away from said base wall, said base wall being integrally coupled to a free end of said proximal portion, said arms of said bent head portion being orientated generally perpendicular to a longitudinal axis of said arm, said bent head portion having a pair of outer perimeter edges, each of said outer perimeter edges having an elongate slot therein, each of said slots in said outer perimeter edges extending from said free end of said proximal portion and around a free end of said arms; and a second securing means releasably secures a portion of floss in said slots in said arms;

wherein said distal, middle, and proximal portions of said arm each have opposite sides defining a height between said opposite sides, the height of said distal and proximal portions being substantially equal, the height of said middle portion being approximately twice the height of said distal and proximal portions such that both of the opposite sides of said middle portion protrude with respect to each of the opposite sides of said distal and proximal portions.

2. The tooth flossing device as in claim 1, wherein said distal portion is in an angular relationship with said middle portion such that an angle formed between said top sides of said middle and distal portions is generally between 150 degrees and 175 degrees.

3. The tooth flossing device as in claim 1, wherein said legs of said straight head portion are orientated generally parallel to a longitudinal axis of said arm.

4. The tooth flossing device as in claim 3, wherein each of said legs of said straight head portion have a generally rounded free end, each of said slots extending from said free end of said distal portion and around a free end of said legs.

5. The tooth flossing device as in claim 1, wherein each of said arms generally lie in a plane of said proximal portion, each of said arms having a generally rounded free end.

6. The tooth flossing device as in claim 1, wherein each of said first and second securing means comprises a protruding member, said protruding member being securely attached to said top side of said arm, said protruding member being positioned generally adjacent to said straight head portion, said protruding member having a top end having a channel therein for releasably engaging the floss.

7. A tooth flossing device for holding a portion of tooth floss, said device comprising:

an arm, said arm having a middle portion, a distal portion and a proximal portion, said arm having a top side and a bottom side, said distal portion being in an angular relationship with said middle portion such that an angle formed between said top sides of said middle and distal portions is generally between 150 degrees and 175 degrees, said middle portion having a relatively greater height than said distal and proximal portions, wherein said distal, middle, and proximal portions of said arm each have opposite sides defining a height between said opposite sides, the height of said distal and proximal portions being substantially equal, the height of said middle portion being approximately twice the height of said distal and proximal portions such that both of the opposite sides of said middle portion protrude with respect to each of the opposite sides of said distal and proximal portions;

a straight head portion, said straight head portion comprising a base portion and two legs integrally coupled to and extending away from said base portion, said straight head portion being generally U-shaped, said base portion being integrally coupled to a free end of said distal portion, said legs of said straight head portion being orientated generally parallel to a longitudinal axis of said arm, each of said legs having a generally rounded free end, said straight head portion having a pair of outer peripheral edges, each of said outer peripheral edges having an elongate slot therein, each of said slots extending from said free end of said distal portion and around a free end of said legs;

a bent head portion, said bent head portion comprising a base wall and two arms integrally coupled to and extending away from said base wall, said bent head portion generally being a U-shaped, said base wall being integrally coupled to a free end of said proximal portion, said arms of said bent head portion being orientated generally perpendicular to a longitudinal axis of said arm, each of said arms generally lying in a plane of said proximal portion, each of said arms having a generally rounded free end, said bent head portion having a pair of outer perimeter edges, each of said outer perimeter edges having an elongate slot therein, each of said slots in said outer perimeter edges extending from said free end of said proximal portion and around a free end of said arms; and a securing means for releasably securing said floss in said bent and straight heads, said securing means comprising a pair of protruding members, each of said protruding members being securely attached to said top side of said arm, each of said protruding members being positioned generally adjacent to one of said heads, each of said protruding members having a top end having a channel therein for releasably engaging the floss.

8. A method of flossing teeth using tooth floss comprising the steps of:

providing an arm, said arm having a middle portion, a distal portion and a proximal portion, said arm having a top side and a bottom side, said distal portion being in an angular relationship with said middle portion such that an angle formed between said top sides of said middle and distal portions is generally between 150 degrees and 175 degrees, wherein said distal, middle, and proximal portions of said arm each have opposite sides defining a height between said opposite sides, the height of said distal and proximal portions being substantially equal, the height of said middle portion being approximately twice the height of said distal and proximal portions such that both of the opposite sides of said middle portion protrude with respect to each of the opposite sides of said distal and proximal portions;

providing a straight head portion, said straight head portion comprising a base portion and two legs integrally coupled to and extending away from said base portion, said base portion being integrally coupled to a free end of said distal portion, said legs of said straight head portion being orientated generally parallel to a longitudinal axis of said arm, said straight head portion having a pair of outer peripheral edges, each of said outer peripheral edges having an elongate slot therein, each of said slots extending from said free end of said distal portion and around a free end of said legs;

providing a bent head portion, said bent head portion comprising a base wall and two arms integrally coupled to and extending away from said base wall, said base wall being integrally coupled to a free end of said proximal portion, said arms of said bent head portion being orientated generally perpendicular to a longitudinal axis of said arm, said bent head portion having a pair of outer perimeter edges, each of said outer perimeter edges having an elongate slot therein, each of said slots in said outer perimeter edges extending from said free end of said proximal portion and around a free end of said arms, a distance between said arms being generally between ½ and ¾ inches;

providing a securing means for releasably securing said floss in said bent and straight head portions, said securing means comprising a pair of protruding members, each of said protruding members being securely attached to said top side of said arm, each of said protruding members being positioned generally adjacent to one of said head portions, each of said protruding members having a top end having a channel therein for releasably engaging the floss;

wrapping each of a pair of floss portions about a pair of oppositely disposed slots on one of said head portions;

placing opposite ends of said floss through a channel in a respective securing means; and flossing said teeth with portions of said floss extending between said free ends of said arms and said legs.

* * * * *